(12) United States Patent
DeWees et al.

(10) Patent No.: US 9,579,223 B2
(45) Date of Patent: Feb. 28, 2017

(54) PROTECTIVE SLEEVE FOR A MEDICAL DEVICE

(71) Applicant: Shriners Hospital For Children, Tampa, FL (US)

(72) Inventors: Todd DeWees, Vancouver, WA (US); Steve Miller, Dallas, OR (US)

(73) Assignee: SHRINERS HOSPITAL FOR CHILDREN, Tampa, FL (US)

( * ) Notice: Subject to any disclaimer, the term of this patent is extended or adjusted under 35 U.S.C. 154(b) by 114 days.

(21) Appl. No.: 14/459,374

(22) Filed: Aug. 14, 2014

(65) Prior Publication Data

US 2015/0051712 A1    Feb. 19, 2015

Related U.S. Application Data

(60) Provisional application No. 61/866,395, filed on Aug. 15, 2013.

(51) Int. Cl.
*A61F 2/62*    (2006.01)
*A61F 2/78*    (2006.01)
(Continued)

(52) U.S. Cl.
CPC ............ *A61F 2/7812* (2013.01); *A41D 27/10* (2013.01); *A61F 2/78* (2013.01); *A61F 5/01* (2013.01);
(Continued)

(58) Field of Classification Search
CPC ............ A61F 2/0059; A61F 2002/5001; A61F 2005/0181; A61F 5/0109; A61F 2/78; A61F 2002/7837; A41D 13/0543; A41D 13/055; A41D 13/0556; A41D 13/06; A41D 13/065; A41D 13/08; A41D 13/088; A41D 17/00; A41D 17/005; A41D 19/01505; A41D 27/10; A41D 27/12; A41D 27/13;
(Continued)

(56) References Cited

U.S. PATENT DOCUMENTS 4,834,079 A * 5/1989 Benckhuijsen .......... A61D 9/00
                                                            54/82
5,592,953 A * 1/1997 Delao .................... A61F 15/004
                                                            128/882
(Continued)

*Primary Examiner* — Christian Sevilla
*Assistant Examiner* — Cheryl Miller
(74) *Attorney, Agent, or Firm* — Baker Botts L.L.P.

(57) ABSTRACT

Protective sleeve for a medical device having a moveable joint including a tubular assembly comprising a flexible material that satisfies International Organization for Standardization ISO13997 (1999) for a cut resistance of at least ISO level 5. The tubular assembly has a first end portion, a second end portion, and a length extending therebetween. The tubular assembly includes a base member made of the flexible material having an internal surface and an external surface and a reinforcing member made of the flexible material coupled to the base member along the internal surface and the external surface of the base member. The reinforcing member forms a channel at the first end portion. The tubular assembly has an internal cross dimension sized to receive a medical device having a moveable joint therein. The protective sleeve further includes an adjustment member received in the channel to radially adjust the first end portion.

23 Claims, 16 Drawing Sheets

(51) Int. Cl.
- *A41D 27/10* (2006.01)
- *A61F 5/01* (2006.01)
- *A41D 13/05* (2006.01)
- *A61F 2/50* (2006.01)
- *A41D 31/00* (2006.01)
- *A41D 17/00* (2006.01)
- *A41D 19/015* (2006.01)

(52) U.S. Cl.
CPC ...... *A41D 13/0543* (2013.01); *A41D 13/0556* (2013.01); *A41D 13/0562* (2013.01); *A41D 13/0575* (2013.01); *A41D 17/005* (2013.01); *A41D 19/01505* (2013.01); *A41D 31/0016* (2013.01); *A41D 31/0055* (2013.01); *A41D 31/0061* (2013.01); *A41D 2300/22* (2013.01); *A41D 2300/32* (2013.01); *A41D 2300/33* (2013.01); *A41D 2300/332* (2013.01); *A41D 2500/10* (2013.01); *A41D 2500/20* (2013.01); *A61F 2002/5001* (2013.01); *A61F 2002/5016* (2013.01); *A61F 2002/5027* (2013.01); *A61F 2002/7837* (2013.01)

(58) Field of Classification Search
CPC ........ A41D 27/16; A41D 27/18; A41D 27/20; A41D 27/201; A41D 27/202; A41D 27/24; A41D 27/245; A41D 31/0011; A41D 31/0016; A41D 31/0055; A41D 31/0061; A41D 2300/30; A41D 2300/322; A41D 2300/33; A41D 2300/332; A41D 2400/00; A41D 2500/20; A41D 2600/00
See application file for complete search history.

(56) References Cited

U.S. PATENT DOCUMENTS

| | | | |
|---|---|---|---|
| 5,800,566 A | 9/1998 | Gramnas | |
| 5,815,948 A | 10/1998 | Dzielak et al. | |
| 6,155,084 A * | 12/2000 | Andrews | A41D 13/08 2/16 |
| 6,199,217 B1 | 3/2001 | Mooney | |
| 6,205,593 B1 | 3/2001 | Schaub | |
| 6,254,988 B1 * | 7/2001 | Zhu | D02G 3/047 428/362 |
| 6,960,175 B1 | 11/2005 | Myers | |
| 7,638,193 B1 * | 12/2009 | Rebouillat | D01D 4/02 428/370 |
| 2002/0174565 A1 * | 11/2002 | Roelofs | A41D 17/00 36/2 R |
| 2004/0011087 A1 * | 1/2004 | Rebouillat | A41D 31/0055 66/174 |
| 2006/0048496 A1 * | 3/2006 | Waggett | A41D 31/0055 57/210 |
| 2007/0162154 A1 | 7/2007 | Scott | |
| 2007/0204373 A1 * | 9/2007 | Loyens | A41D 13/08 2/16 |
| 2009/0076625 A1 * | 3/2009 | Groves | A61F 2/7812 623/34 |
| 2009/0275253 A1 * | 11/2009 | Hahn | D02G 3/047 442/181 |
| 2011/0131706 A1 * | 6/2011 | Andersson | A41B 11/02 2/239 |
| 2011/0237146 A1 * | 9/2011 | Zumloh-Nebe | D02G 3/04 442/308 |
| 2013/0190895 A1 * | 7/2013 | Kristinsdottir | A61F 2/7812 623/36 |
| 2013/0315672 A1 * | 11/2013 | Pajak | F16L 1/028 405/157 |
| 2014/0137304 A1 * | 5/2014 | Katz | A41D 13/081 2/16 |
| 2014/0371872 A1 * | 12/2014 | Sawatzki | A61F 2/50 623/27 |

\* cited by examiner

PROTECTIVE SLEEVE FOR A MEDICAL DEVICE

CROSS-REFERENCE TO RELATED APPLICATION

This application claims priority to U.S. Provisional Patent Application Ser. No. 61/866,395, filed Aug. 15, 2013, which is incorporated by reference herein in its entirety.

BACKGROUND OF THE DISCLOSED SUBJECT MATTER

Field of the Disclosed Subject Matter

The disclosed subject matter relates to a protective sleeve for a medical device, such as a prosthetic or an orthotic.

Description of the Related Art

Medical devices, such as prosthetics and orthotics, are commonly used throughout the medical industry. Often times, medical devices are worn underneath clothing. For example, an individual may have a prosthetic leg with a movable knee joint which conveniently fits within conventional clothing, such as pants or the like. Unfortunately, a drawback of with some prosthetics is that the outer clothing, such as pants, catches within the movable knee joint. Such instances can unnecessarily wear the movable joint and even damage the joint, which can be extremely expensive to repair or replace. Furthermore, often the clothing is abraded or even punctured by the engagement of the movable joint with the clothing. The quick abrasion, cutting, and tearing of clothing requires individuals to purchase clothing more frequently than individuals without medical devices.

Thus there remains a continued need for an efficient and economic system for a protective sleeve for a medical device. The presently disclosed subject matter satisfies these and other needs.

SUMMARY OF THE DISCLOSED SUBJECT MATTER

The purpose and advantages of the disclosed subject matter will be set forth in and are apparent from the description that follows, as well as will be learned by practice of the disclosed subject matter. Additional advantages of the disclosed subject matter will be realized and attained by the devices particularly pointed out in the written description and claims hereof, as well as from the appended drawings.

To achieve these and other advantages and in accordance with the purpose of the disclosed subject matter, as embodied and broadly described, the disclosed subject matter includes a protective sleeve for a medical device having a moveable joint. The protective sleeve includes a tubular assembly comprising a flexible material that satisfies International Organization for Standardization ISO13997 (1999) for a cut resistance of at least ISO level 5. The tubular assembly has a first end portion, a second end portion, and a length extending therebetween. The tubular assembly includes a base member made of the flexible material having an internal surface and an external surface and a reinforcing member made of the flexible material coupled to the base member along the internal surface and the external surface of the base member. The reinforcing member forms a channel at the first end portion of the tubular assembly. The tubular assembly has an internal cross dimension sized to receive a medical device having a moveable joint therein. The protective sleeve further includes an adjustment member received in the channel to radially adjust the first end portion of the tubular assembly.

In accordance with another aspect of the disclosed subject matter, method of making a protective sleeve for a medical device having a movable joint is disclosed. A base member is provided comprising a flexible material that satisfies International Organization for Standardization ISO13997 (1999) for cut resistance of at least ISO level 5, the base member has an internal surface and an external surface. A reinforcing member made of the flexible material is coupled to the base member along the internal surface and the external surface of the base member to form a channel. A tubular assembly is formed with the base member and the reinforcing member, the tubular assembly having a first end portion and a second end portion and a length extending therebetween. The channel is disposed at the first end portion of the tubular assembly, the tubular assembly further has an internal cross dimension sized to receive a medical device having a movable joint therein. An adjustment member is inserted within the channel to adjust radially the first end portion of the tubular assembly.

In accordance with a further aspect of the disclosed subject matter, a protective sleeve system is provided comprising a medical device including a member and a moveable joint coupled to the base. The system further includes a protective sleeve comprising a tubular assembly comprising a flexible material that satisfies International Organization for Standardization ISO13997 (1999) for a cut resistance of at least ISO level 5, the tubular assembly having a first end portion, a second end portion, and a length extending therebetween. The tubular assembly includes a base member made of the flexible material having an internal surface and a external surface and a reinforcing member made of the flexible material coupled to the base member along the internal surface and the external surface of the base member. The reinforcing member forms a channel at the first end portion of the tubular assembly. The tubular assembly having an internal cross dimension sized to receive a medical device having a moveable joint therein. The protective sleeve further having an adjustment member received in the channel to radially adjust the first end portion of the tubular assembly, wherein the length of the tubular assembly is sufficient to extend beyond the moveable joint and the reinforcing member is aligned with the moveable joint when the first end portion of the tubular assembly is in engagement with the member of the medical device.

It is to be understood that both the foregoing general description and the following detailed description and drawings are examples and are provided for purpose of illustration and not intended to limit the scope of the disclosed subject matter in any manner.

The accompanying drawings, which are incorporated in and constitute part of this specification, are included to illustrate and provide a further understanding of the devices of the disclosed subject matter. Together with the description, the drawings serve to explain the principles of the disclosed subject matter.

BRIEF DESCRIPTION OF THE DRAWINGS

The subject matter of the application will be more readily understood from the following detailed description when read in conjunction with the accompanying drawings, in which.

DETAILED DESCRIPTION

Reference will now be made in detail to embodiments of the disclosed subject matter, an example of which is illustrated in the accompanying drawings. The disclosed subject matter will be described in conjunction with the detailed description of the system.

As disclosed herein, the protective sleeve and system presented herein can be used in combination with a medical device, such as for example, a prosthetic device or orthotic device.

In accordance with the disclosed subject matter, a protective sleeve for a medical device having a moveable joint is provided. The protective sleeve includes a tubular assembly comprising a flexible material that satisfies International Organization for Standardization ISO13997 (1999) for a cut resistance of at least ISO level 5. The tubular assembly has a first end portion, a second end portion, and a length extending therebetween. The tubular assembly includes a base member made of the flexible material having an internal surface and an external surface and a reinforcing member made of the flexible material coupled to the base member along the internal surface and the external surface of the base member. The reinforcing member forms a channel at the first end portion of the tubular assembly. The tubular assembly has an internal cross dimension sized to receive a medical device having a moveable joint therein. The protective sleeve further includes an adjustment member received in the channel to radially adjust the first end portion of the tubular assembly.

In accordance with a further aspect of the disclosed subject matter, a protective sleeve system is provided comprising a medical device including a member and a moveable joint coupled to the base. The system further includes a protective sleeve comprising a tubular assembly comprising a flexible material that satisfies international Organization for Standardization ISO13997 (1999) for a cut resistance of at least ISO level 5, the tubular assembly having a first end portion, a second end portion, and a length extending therebetween. The tubular assembly includes a base member made of the flexible material having an internal surface and an external surface and a reinforcing member made of the flexible material coupled to the base member along the internal surface and the external surface of the base member. The reinforcing member forms a channel at the first end portion of the tubular assembly. The tubular assembly having an internal cross dimension sized to receive a medical device having a moveable joint therein. The protective sleeve further having an adjustment member received in the channel to radially adjust the first end portion of the tubular assembly, wherein the length of the tubular assembly is sufficient to extend beyond the moveable joint and the reinforcing member is aligned with the moveable joint when the first end portion of the tubular assembly is in engagement with the member of the medical device.

Figure 1:
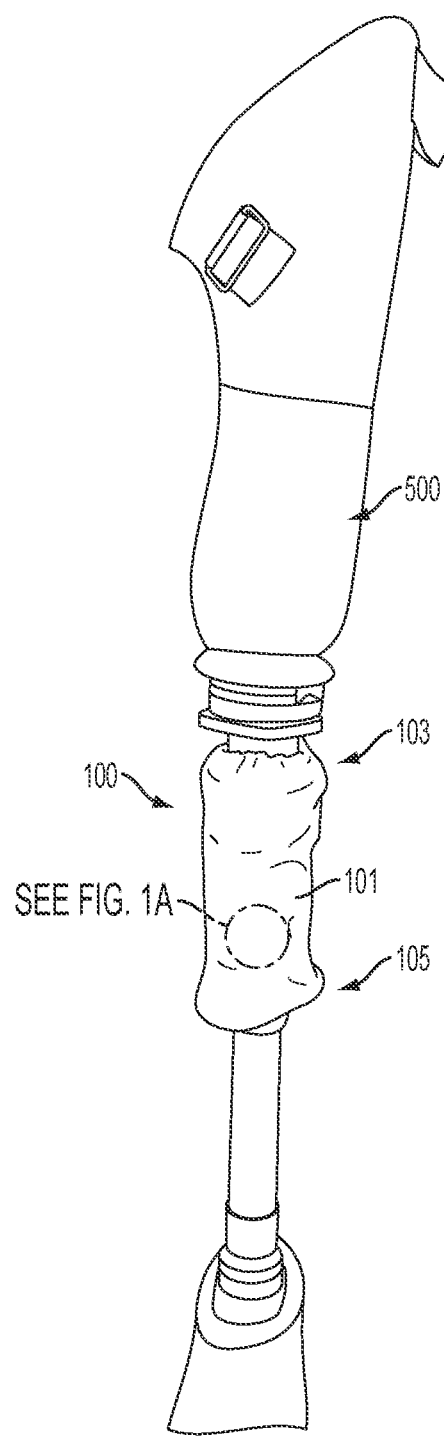
FIG. 1 is an image of an exemplary embodiment of a protective sleeve system on a prosthetic leg, according to an embodiment of the disclosed subject matter for purposes of illustration and not limitation.

Solely for purpose of illustration, an exemplary embodiment of a protective sleeve system with a prosthetic leg, is shown schematically in FIG. 1. As illustrated, FIG. 1 depicts a protective sleeve 100 for a medical device 500 having a movable joint. As embodied in FIG. 1, the medical device 500 is a prosthetic device for a prosthetic knee that is protected with the protective sleeve 100, for purposes of illustration. However, the medical device 500 can comprise any suitable medical device including, but not limited to, a prosthetic and an orthotic. Examples of prosthetics include, but are not limited to, prosthetic knees and/or elbows and an example of an orthotic device, includes, but is not limited to, a brace such as a knee brace. The examples herein therefore are not intended to limit the scope of the disclosed subject matter in any manner. The protective sleeve 100 comprises a tubular assembly 101 and an adjustment member, which will be further described herein in detail.

As depicted in FIG. 1, the tubular assembly 101 has a first end portion 103, a second end portion 105, and a length extending therebetween. The tubular assembly comprises a flexible material that satisfies standard ISO 13997:1999 of the International Organization for Standardization (ISO) for a cut resistance of at least ISO level 5. As known in the industry, the ISO develops International Standards for products, services, and goods practice. The standard ISO 13997:1999 provides specifications for the determination of resistance to cutting by sharp objects and the mechanical properties associated with protective clothing. Level 5 of standard ISO 13997:1999 specifies that the material must be able to resist at least +22.0 N of force prior to a failure of the material. As embodied herein, the tubular assembly comprises a flexible material that satisfies standard ISO 13997:1999 for a cut resistance of at least ISO level 5.

According to other embodiments of the disclosed subject matter, the material of the tubular assembly also at least meets European Standard EN 388 (2003) testing threshold for an abrasion resistance of at least level 4 and a tear resistance of at least level 4. As known in the industry, European Standards are an expression of requirements for products, processes or services to meet the requirement of fitness for a particular purpose in Europe. European Standard EN 388 (2003) outlines the standard applied to all kinds of protective gloves in respect of physical and mechanical aggressions caused by abrasion, blade cut, puncture and tearing in Europe. The abrasion resistance of at least level 4 of EN 388 (2003) specifies that a material must be able to resist at least 8000 cycles prior to abrasion through a given material. The tear resistance of at least level 4 of EN 388 (2003) specifies that a material must be able to resist at least a force of 75 Newton prior to any tearing of the material. Thus, the material of the tubular assembly comprises at least one of cut resistant fabric and tear resistant fabric.

Figure 1A:
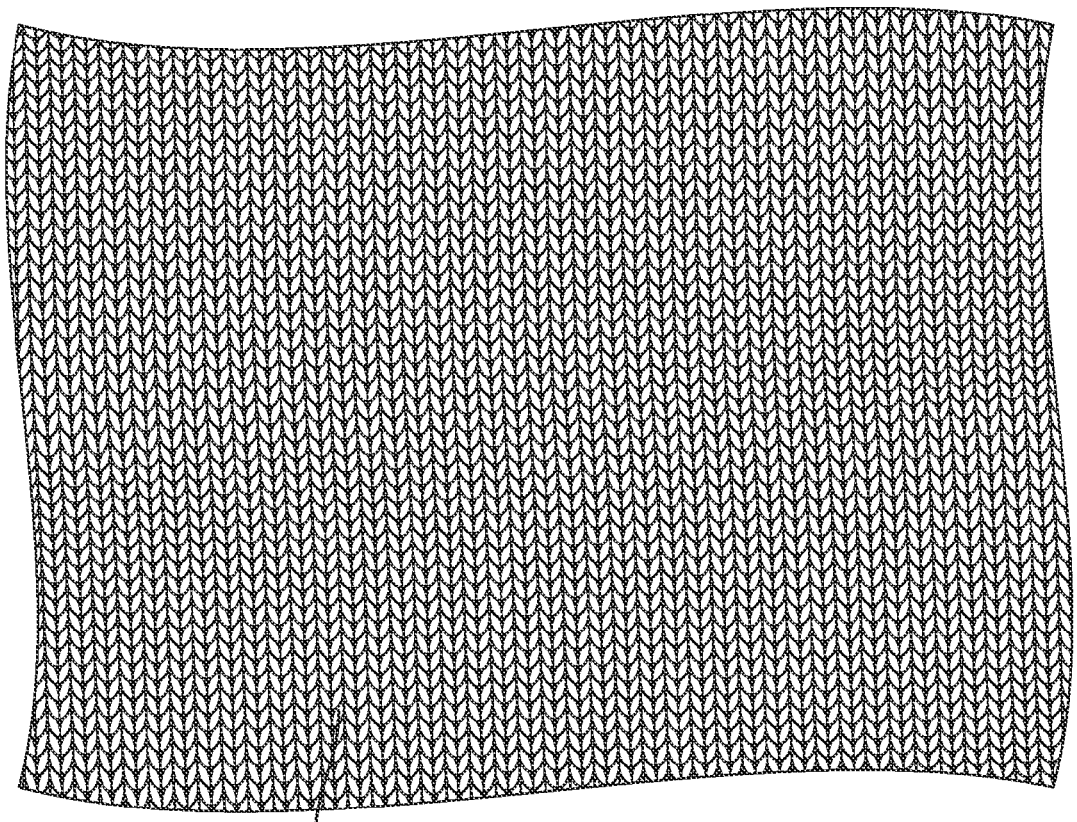
FIG. 1A depicts a magnified view of the material of the tubular assembly of FIG. 1, according to an embodiment of the disclosed subject matter.

For purposes of example, the material of the tubular assembly can comprise ultra-high molecular weight polyethylene. Other suitable materials are further contemplated herein, including, but not limited to, Cut-Tex® PRO cut resistant fabric, manufactured by PPSS Group of the United Kingdom. FIG. 1A depicts a magnified view of the material of the tubular assembly 101 of FIG. 1. As depicted, the material has a woven pattern but can include other suitable configurations.

Figure 2:
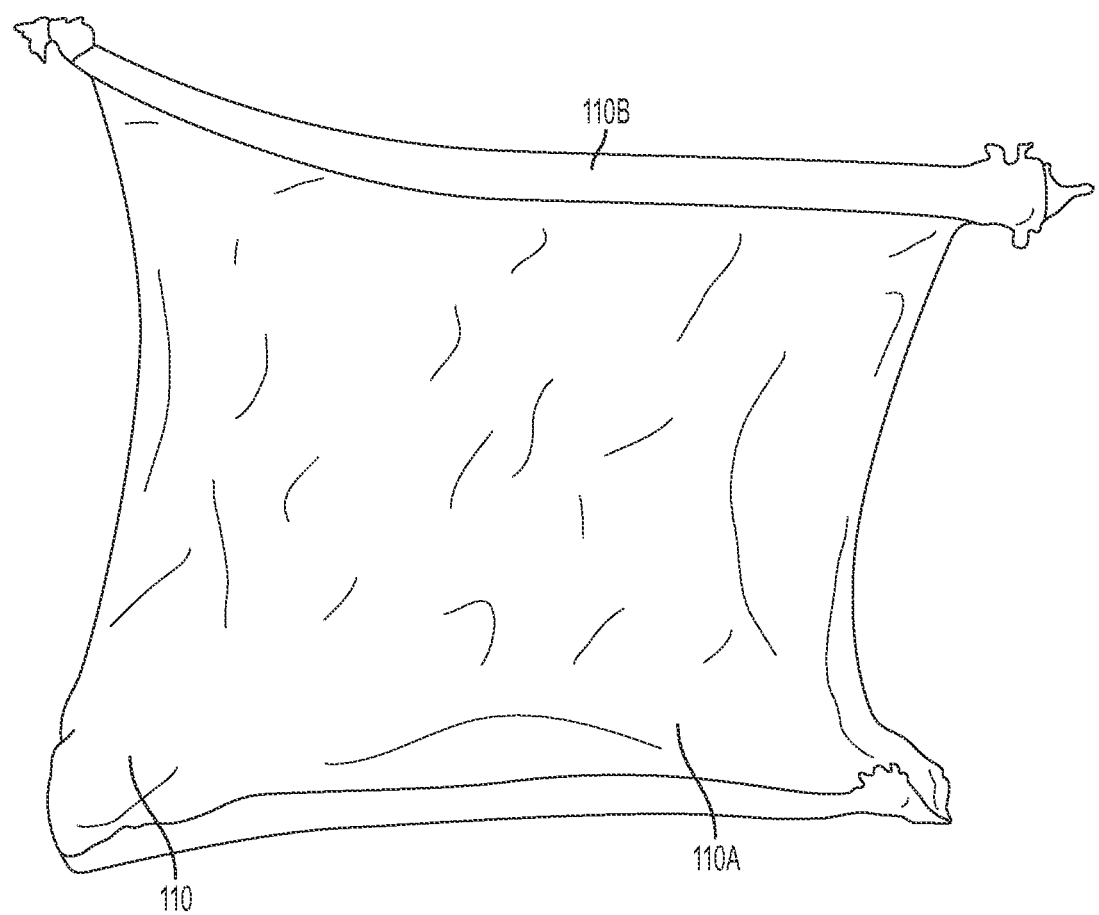
FIG. 2 is an image of an exemplary base member for a tubular assembly, according to an embodiment of the disclosed subject matter.

The tubular assembly includes a base member and a reinforcing member. As embodied in FIG. 2, a base member 110 of the tubular assembly is depicted. The base member is made of the flexible material that at least satisfies standard ISO 13997:1999 for a cut resistance of at least ISO level 5 and has an internal surface 110A and an external surface 110B.

Figure 3:
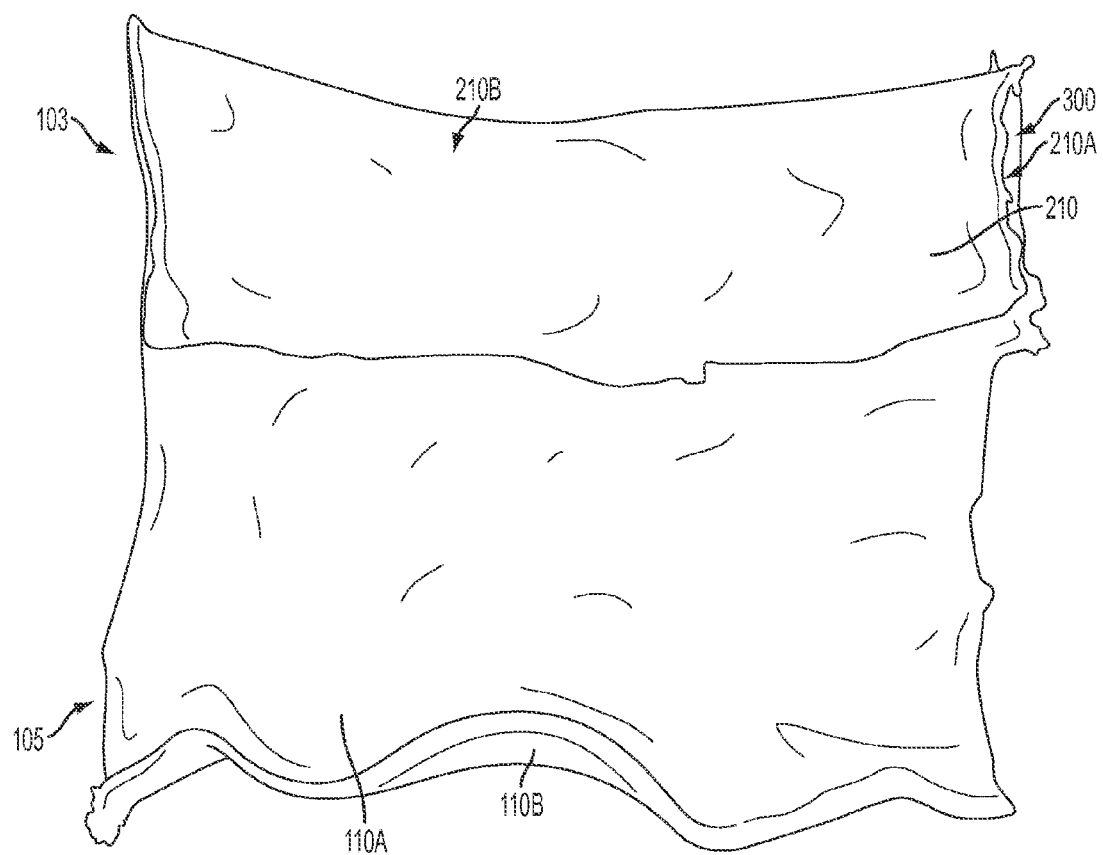
FIG. 3 is an image of the exemplary base member of FIG. 2 coupled with the reinforcing member, according to an embodiment of the disclosed subject matter.

As depicted in FIG. 3, the tubular assembly 101 further includes a reinforcing member 210 coupled to the base member 110. The reinforcing member 210 is also made flexible material that satisfies standard ISO 13997:1999 for a cut resistance of at least ISO level 5. The flexible material of the reinforcing member can be the same or different from the flexible material of the base member as long as the material satisfies standard ISO 13997:1999 for a cut resistance of at least ISO level 5.

As embodied herein, the reinforcing member 210 is coupled to the base member 110 along the internal surface 110A and the external surface 110B of the base member so that the reinforcing member 210 forms a channel 300 at the first end portion 103 of the tubular assembly. The reinforcing member 210 can have an interior surface 210A and an exterior surface 210B such that the interior surface 210A is coupled to both the internal surface 110A and the external surface 110B of the base member 110, as shown in FIG. 3. Other configurations of coupling the reinforcing member with the base member to form a channel are further contemplated herein. For example, the base member can form a channel at a top portion thereof and a reinforcing member can be coupled beneath the channel. In this example, the reinforcing member can be folded to provide a double layer of protection with respect to the medical device, as further discussed herein.

The reinforcing member 210 can be coupled to the base member 110 in a plurality of suitable methods. For purposes of example, the reinforcing member 210 can be sewn to the base member 110 with a heavy grade thread, such as 16 gauge nylon thread, using a standard industrial sewing machine. Other methods, such as adhesive, thermal bonding, weaving, stapling, and the like are furthermore contemplated herein. The reinforcing member 210 can be coupled to the base member 110 about a seam or a substantial portion of the interior surface 210A can be in engagement with a substantial portion of the internal surface 110A and the external surface 110B of the base member 110.

Figure 4:
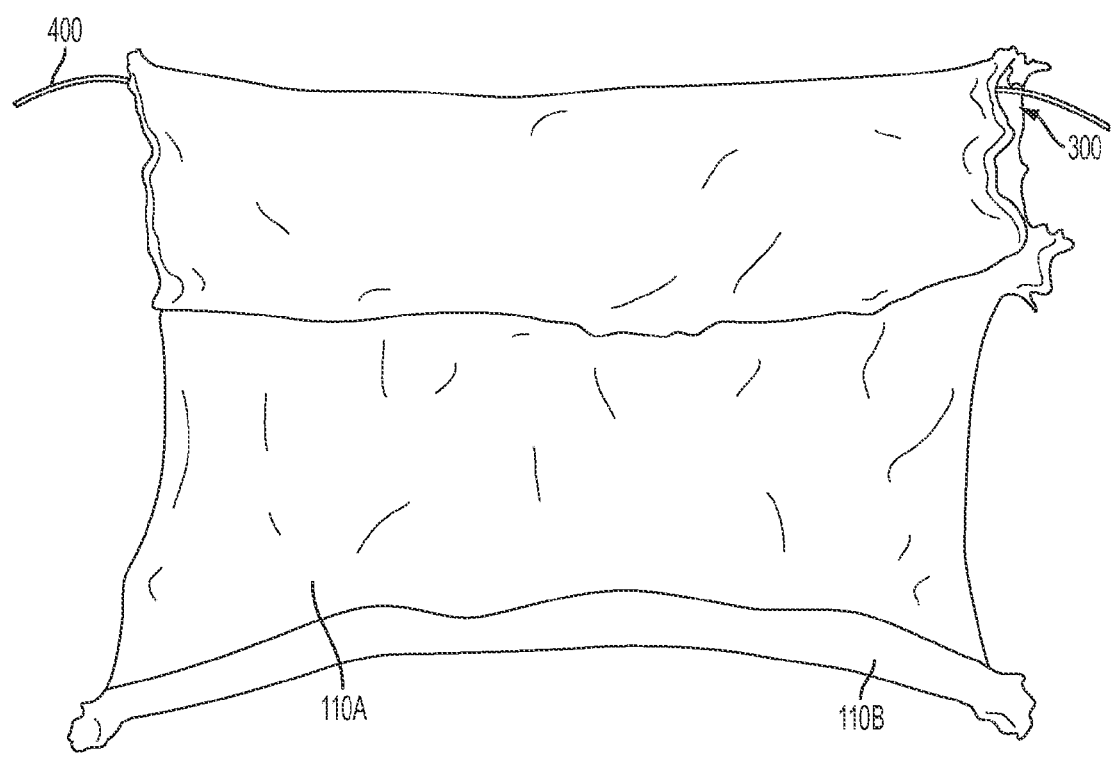
FIG. 4 is an image of the base member and reinforcing member of FIG. 3 defining a channel and having an adjustment member disposed within the channel, according to an embodiment of the disclosed subject matter.

As depicted in FIG. 4, the protective sleeve 100 further includes an adjustment member 400. The adjustment member 400 is received in the channel 300 to radially adjust the first end portion of the tubular assembly, as further discussed herein. The adjustment member can be any suitable device. For example, the adjustment member can comprise a nylon cord, such as Spectrolon®, as depicted in FIG. 4. Other suitable materials for the cord include, but are not limited to, cotton, textured polyester, spun polyester, nylon, polypropylene, and fluoropolymer. Furthermore, other suitable devices for the adjustment member include, but are not limited to, reinforced elastic web, Velcro device, hook and eye arrangement, draw string, fastening device, latch, clasp, or the like that is sufficient to withstand abrasion, cutting, and/or tearing as described herein. In an embodiment, the adjustment member 400 is self-adjustable with the medical device 500, such as, for example a reinforced elastic web.

Figure 5:
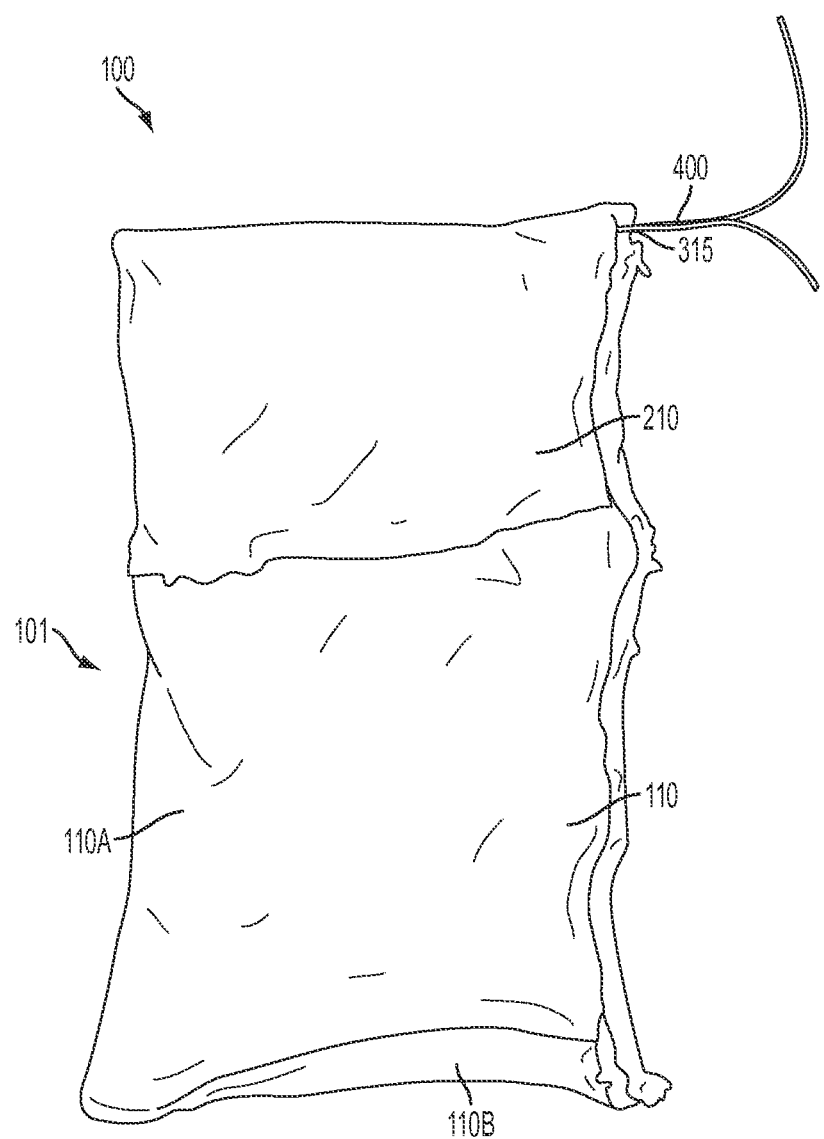
FIG. 5 is an image of the protective sleeve on a flat surface inverted with the internal surface of the base member of FIG. 4 in view, according to an embodiment of the disclosed subject matter.
Figure 6:
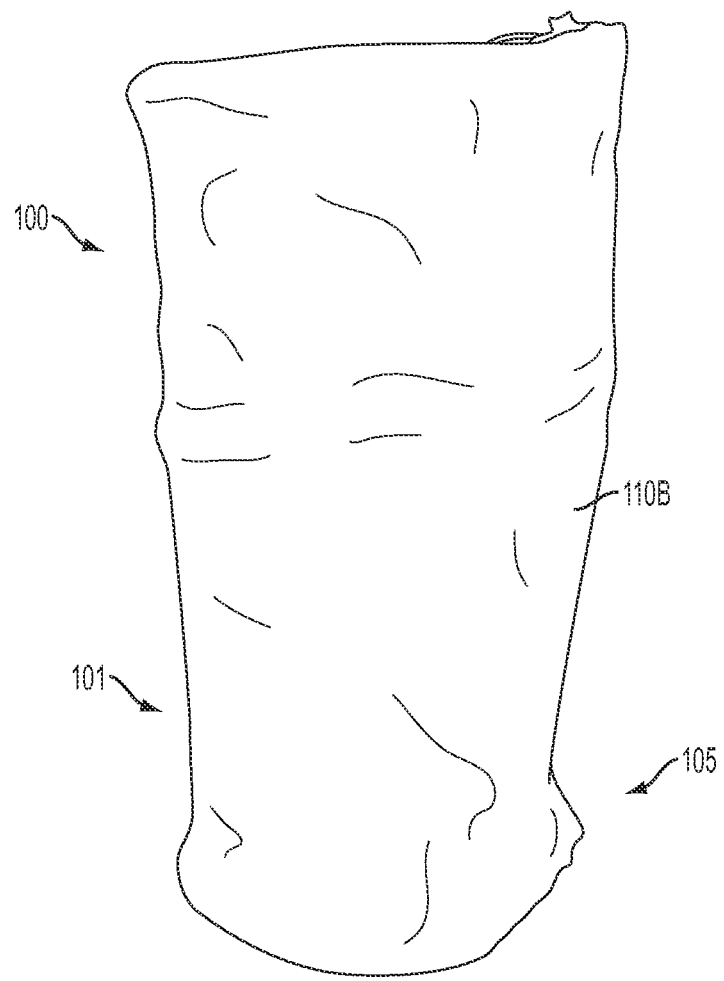
FIG. 6 is an image of the protective sleeve of FIG. 5 upright with the external surface of the base member in view, according to an embodiment of the disclosed subject matter.

As illustrated in FIG. 5, the base member 110 and the reinforcing member 210 are coupled together along a longitudinal side of the base member 110 to form the tubular assembly 101 of the protective sleeve 100. However, the tubular assembly 101 is formed such that the channel 300 includes at least one recess 315 for access to the adjustment member 400 for adjusting a transverse dimension of the first end portion of the tubular assembly, as further explained herein. In FIG. 5, the protective sleeve 100 is pictured lying on a flat surface with the internal surface 110A of the base member in view. FIG. 6 depicts the protective sleeve 100 of FIG. 5 with the external surface 110B in view, with protective sleeve 100 supported by the second end portion 105 of the tubular assembly 101.

Figure 7:
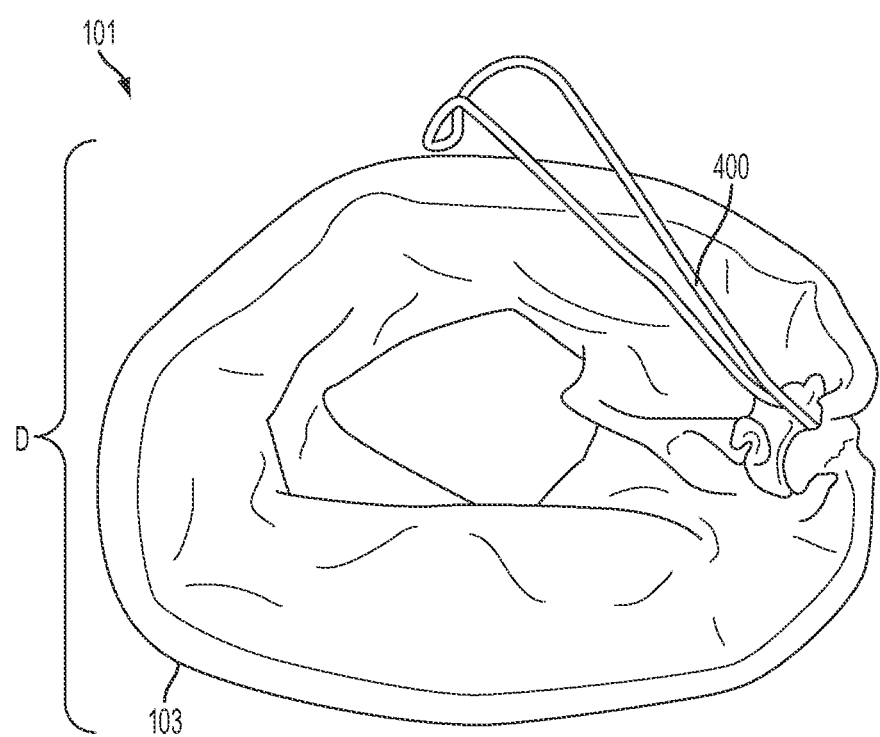
FIG. 7 is a top view of the protective sleeve of FIG. 6 taken from the first end portion of the tubular assembly, according to an embodiment of the disclosed subject matter.

FIG. 7 is a top view of the protective sleeve 100 of FIG. 6 taken from the first end portion 103 of the tubular assembly 101. As depicted, the tubular assembly 101 has an internal cross dimension D sized to receive a medical device having a moveable joint therein. For purposes of example, the internal cross dimension D can have an initial circumference ranging from approximately 7 cm to approximately 25 cm when in a substantially cylindrical configuration, as depicted in FIG. 7. In the embodiment of FIG. 7, the tubular assembly comprises substantially the same internal cross dimension D along the length of the tubular assembly, wherein the internal cross dimension at the first end portion is adjustable by the adjustment member. According to an alternate embodiment, however, the tubular assembly narrows in transverse dimension along the length of the tubular assembly from the first end portion toward the second end portion. Such narrowing construction reduces the amount of material used for manufacture of the tubular assembly and thus reduces cost.

Figure 8:
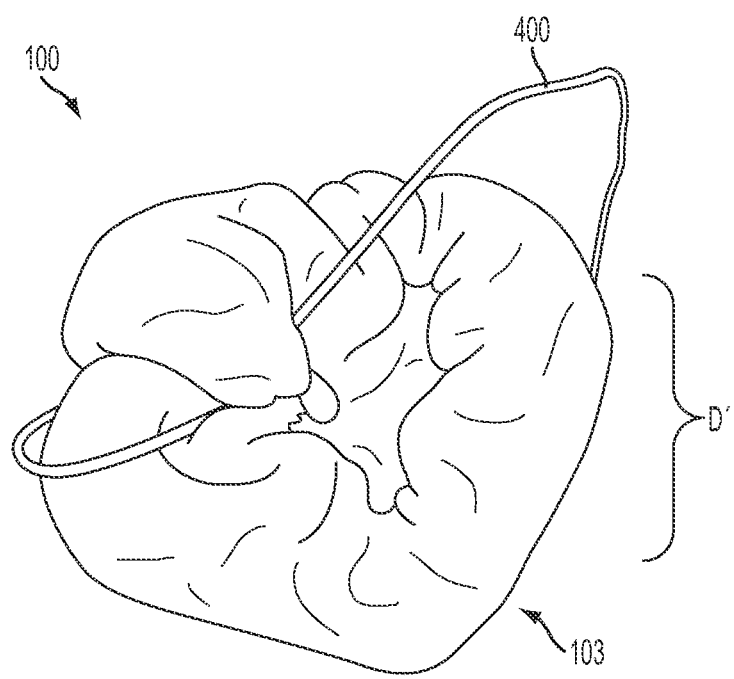
FIG. 8 is a top view of the protective sleeve of FIG. 7 with the adjustment member in an adjusted position, according to an embodiment of the disclosed subject matter.

FIG. 8 is a further top view of the protective sleeve 100 of FIG. 7 with the adjustment member 400 in an adjusted position. In the adjusted position, a transverse dimension of the first end portion 103 of the tubular assembly 101 is adjusted to a dimension D' which is less than the initial diameter of the tubular assembly 101. As illustrated in FIG. 8, the original cross dimension D of the protective sleeve 100 has been reduced to an adjusted cross dimension D'.

Figure 9:
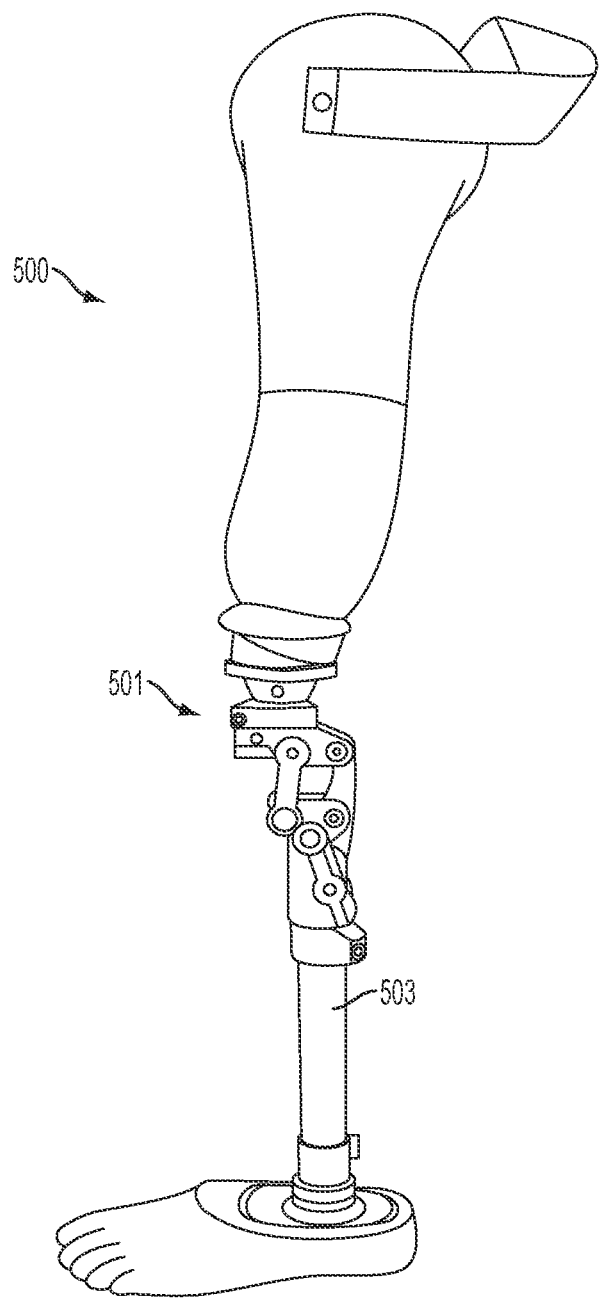
FIG. 9 is a side view of an exemplary medical device for use with the protective sleeve described herein.
Figure 10:
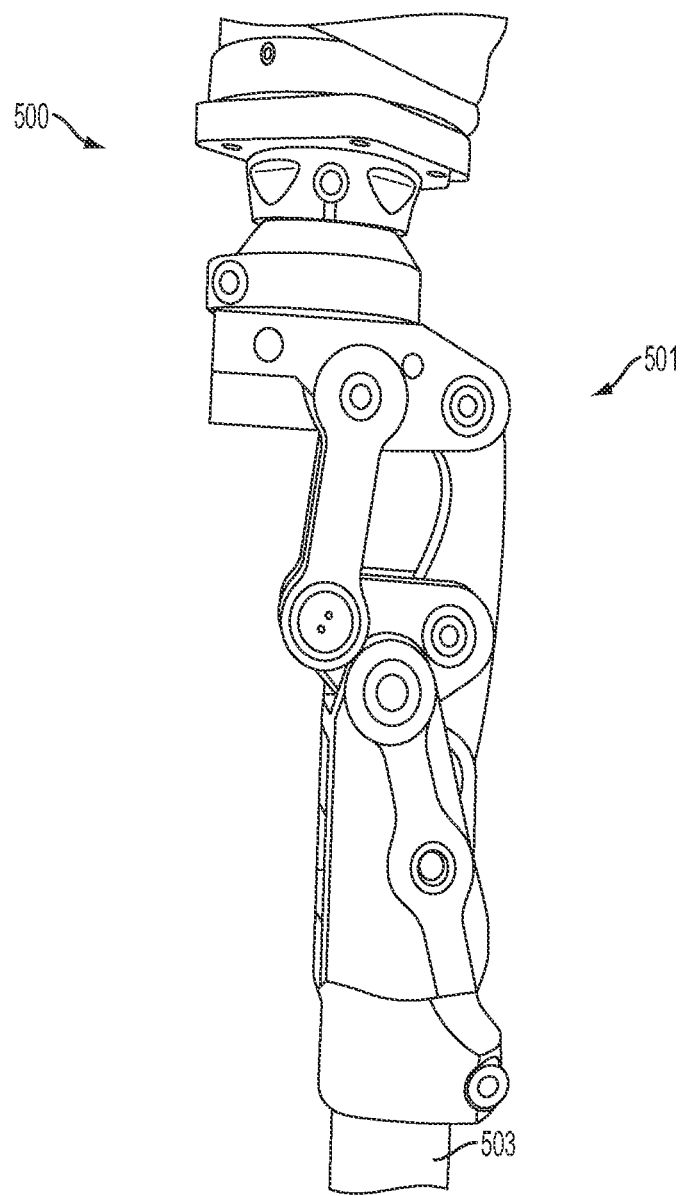
FIG. 10 is an enlarged side view of the movable joint of the medical device of FIG. 9.
Figure 11:
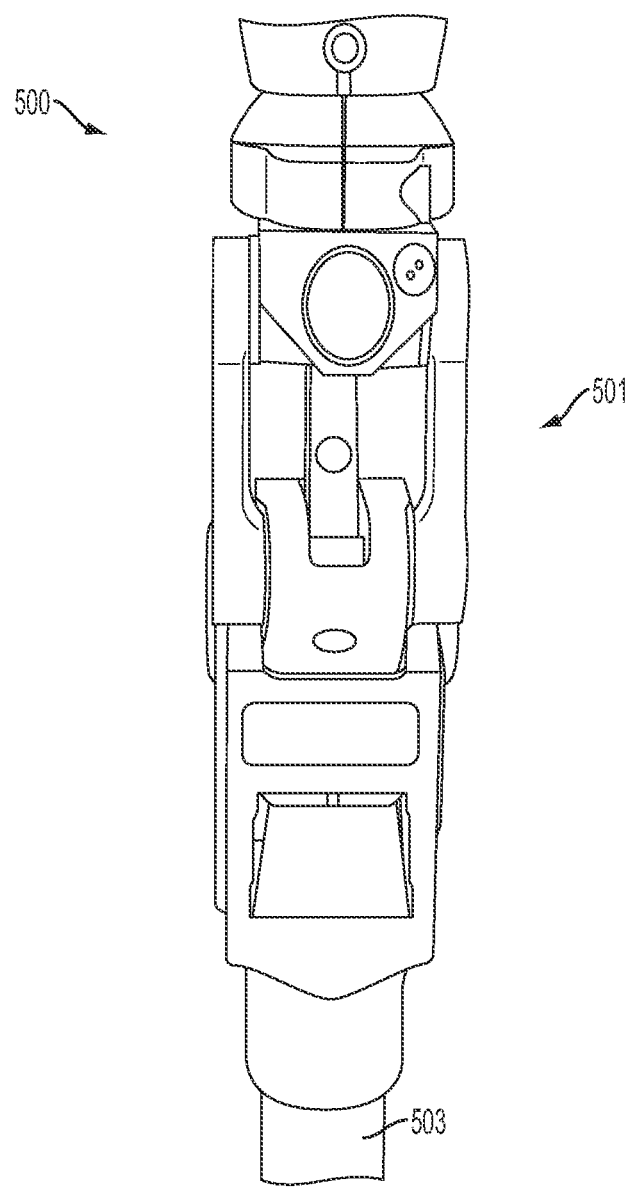
FIG. 11 is a front view of the movable joint of the medical device of FIG. 9.

FIG. 9 illustrates an example of a suitable medical 500 for use with the protective sleeve. In this embodiment, for purposes of example, the medical device 500 is a prosthetic leg having a movable knee joint 501 with a member 503 coupled to the joint 501. The member 503 is coupled to the movable joint 501 at the bottom thereof. FIG. 10 depicts a side view of the movable joint 501 and FIG. 11 depicts a front view of the movable joint 501. An exemplary medical device is disclosed in U.S. Pat. No. 5,800,566 entitled "Artificial joint with a hydraulic damping cylinder", the contents of which are incorporated herein by reference it its entirety.

Figure 12:
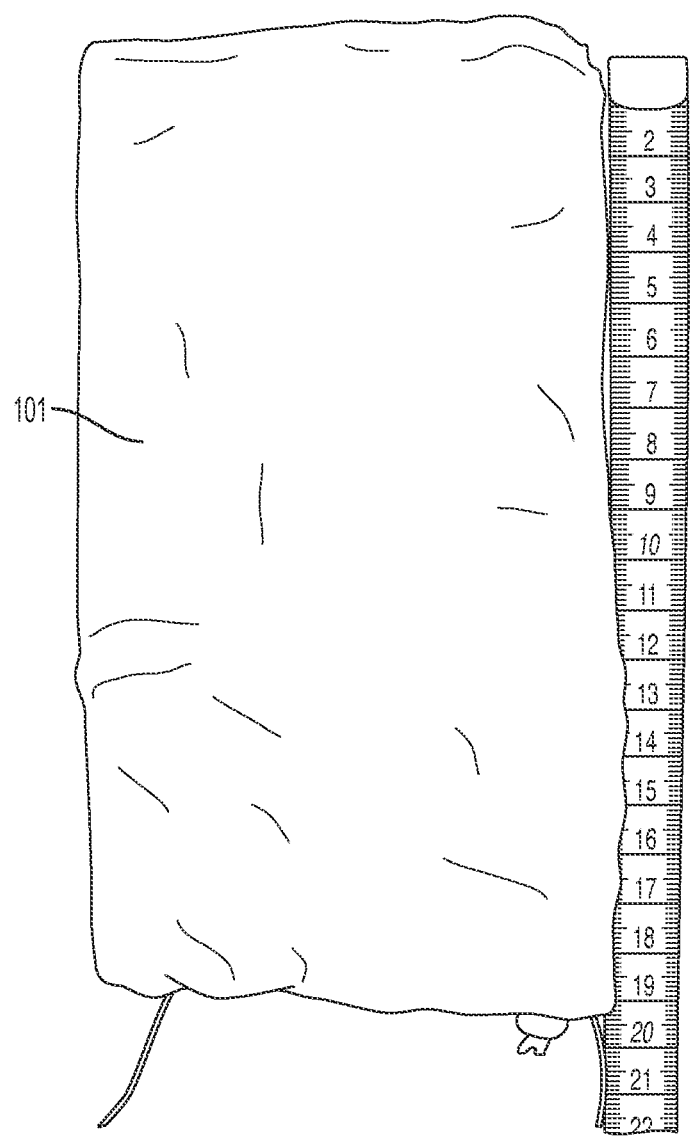
FIG. 12 depicts the protective sleeve on a flat surface with the external surface of the base member of FIG. 4 in view, according to an embodiment of the disclosed subject matter.

With reference to FIG. 1, the protective sleeve 100 is coupled to the medical device 500 above the joint 501 such that the reinforcing member 210 is aligned with the moveable joint 501. The length of the tubular assembly 101 is sufficient to extend beyond the moveable joint 501, as shown. In an embodiment of the disclosed subject matter, the tubular assembly 101 can have a longitudinal dimension ranging from approximately 9 cm to approximately 27 cm, depending on the size of the movable joint. In the embodiment of FIG. 12, for purposes of example, the tubular assembly 101 has a longitudinal dimension of approximately 20 cm.

The reinforcing member can have a longitudinal dimension less than the longitudinal dimension of the tubular assembly. According to an embodiment of the disclosed subject matter, the reinforcing member extends from the first end portion of the tubular assembly toward the second end portion of the tubular assembly to within approximately 50 percent of a longitudinal dimension of the tubular assembly. As shown in the embodiment of FIG. 1, the second end portion 105 of the tabular assembly extends beyond the moveable joint 501 of the medical device and remains unattached to the member 503 of the medical device 500. In other embodiments, such as when the medical device comprises an orthotic such as a brace, the second end portion of the tubular assembly can be attached to the member 503 of the medical device. In either embodiment with an orthotic or a prosthetic, the protective sleeve 100 can be rotatable with respect to the medical device so as to allow the protective sleeve 100 to wear evenly about an inner surface of the protective sleeve 100.

Figure 13A:
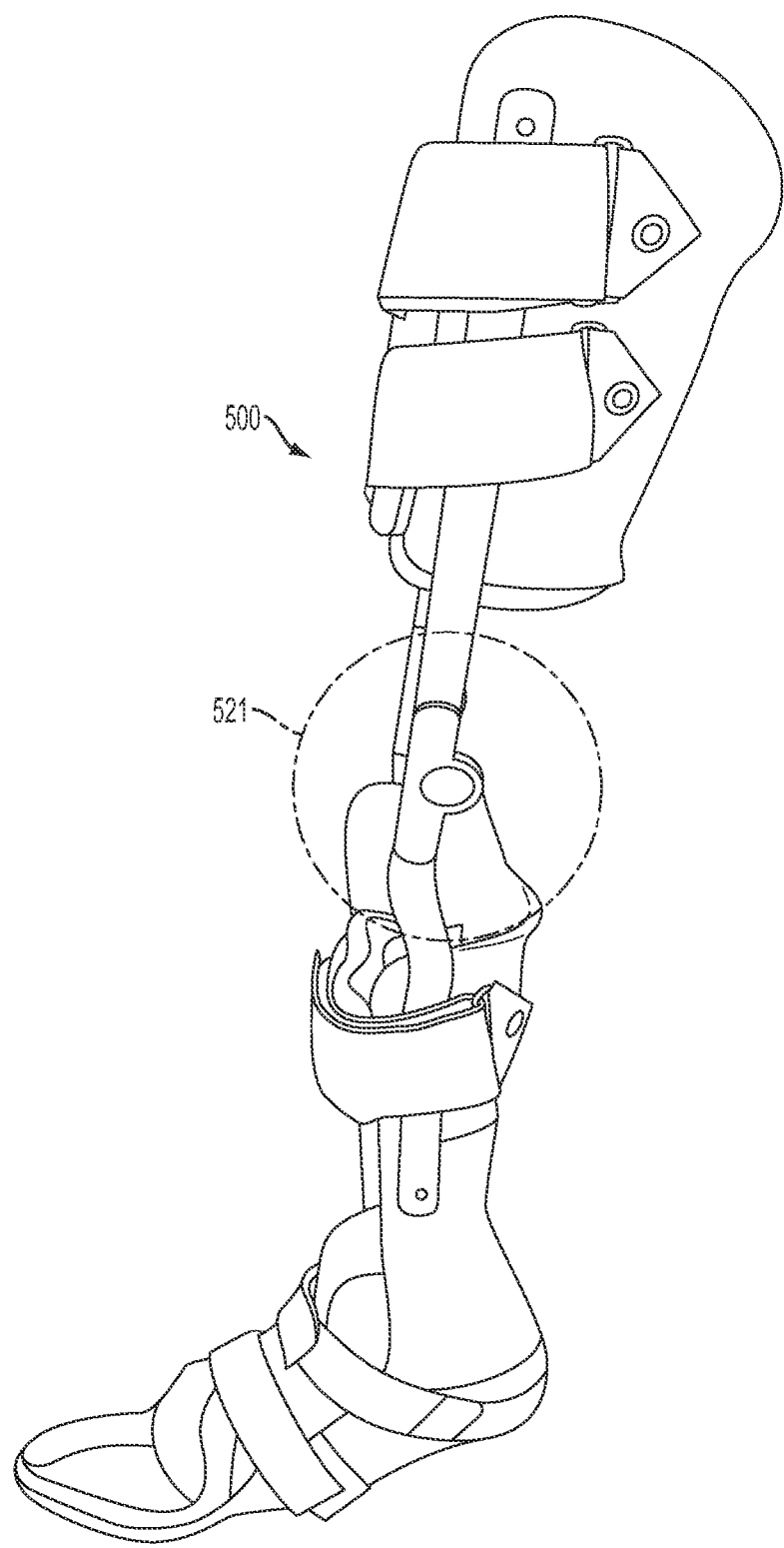
FIG. 13A, FIG. 13B, and FIG. 13C are images of an exemplary medical device and protective sleeve, according to an embodiment of the disclosed subject matter.
Figure 13B:
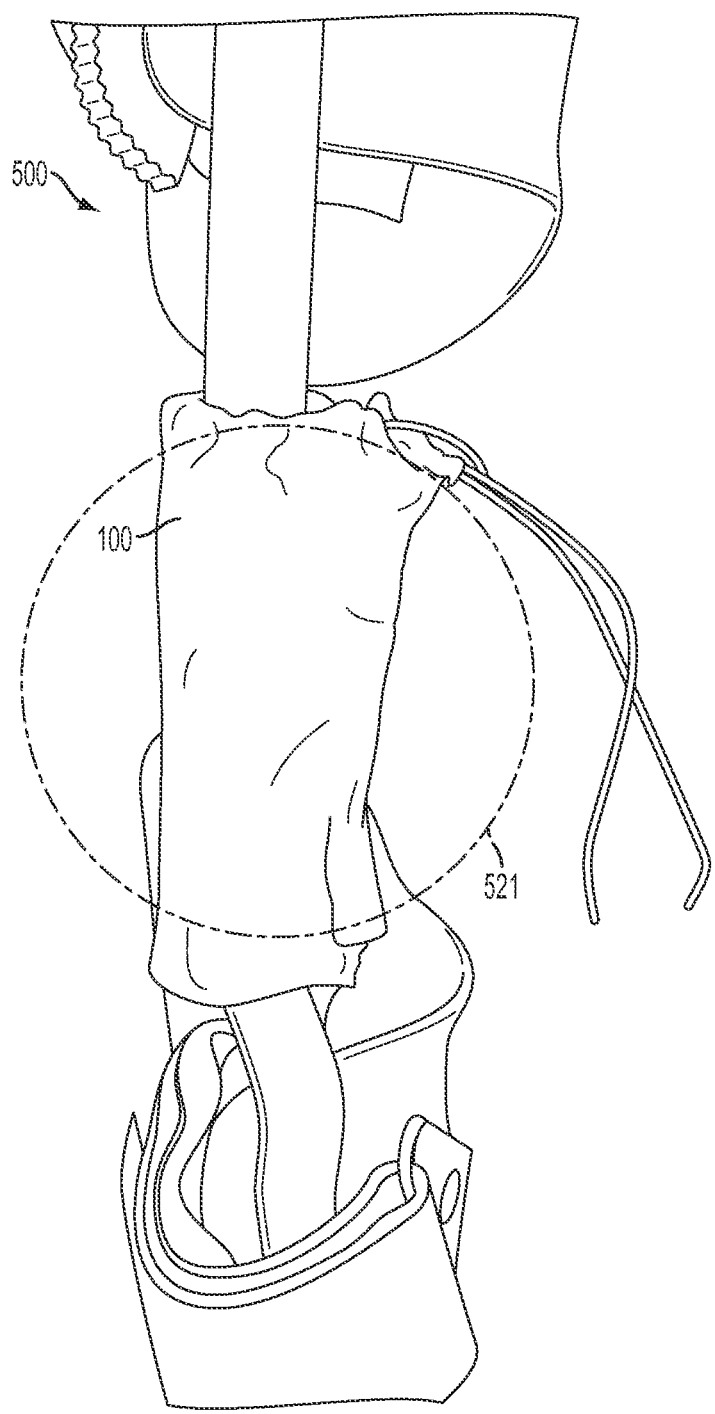
Figure 13C:
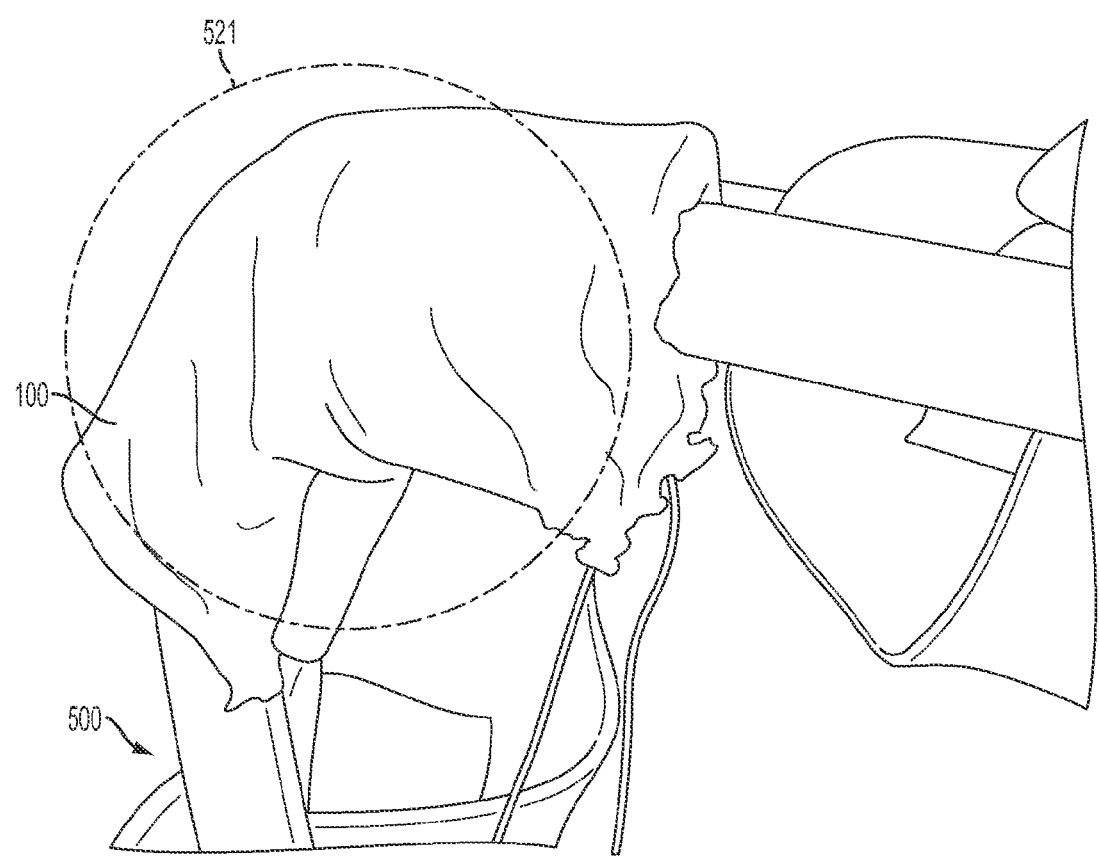

FIG. 13A-13C depict an example of a medical device 500 embodied as an orthotic that is coupleable with a protective sleeve 100. The orthotic medical device 500 of FIG. 13A includes a brace system for a leg which has supporting members at respective longitudinal sides of the brace system. The supporting members respectively include a hinge structure 521 aligned with a knee of a wearer of the orthotic medical device 500. The hinge structure 521 is depicted within the dotted circle of FIG. 13A. As expected, when a wearer of the orthotic medical device 500 bends a knee within the device, the hinge structure 521 of the brace system similarly bends. An exemplary orthotic medical device is disclosed in U.S. Pat. No. 6,960,175 entitled "Orthopedic leg brace", the contents of which are incorporated herein by reference it its entirety.

FIG. 13B depicts the orthotic medical device 500 of FIG. 13A shown coupled with the protective sleeve 100. As shown in FIG. 13B, the protective sleeve 100 is coupled to the orthotic about the hinge structure 521. The hinge structure 521 is positioned in an initial vertically aligned position in FIG. 13B. FIG. 13C depicts the orthotic medical device with the protective sleeve 100 of FIG. 13B with the hinge structure 521 is a second position. The second position represents when a wearer of the orthotic medical device 500 bends a respective knee which causes the hinge structure 521 of the brace system to similarly bend. The protective sleeve 100 remains affixed to the orthotic medical device 500 about the hinge structure 521 in all positions—from the initial position to any subsequent position. The protective sleeve 100 can protect the wearer of the orthotic medical device from any uncomfortable pinching of the skin and can also protect the clothing of the wearer which may be disposed between the wearer and the orthotic medical device. Furthermore, the protective sleeve 100 can also protect the medical device 500 from any unusual wear and tear or unnecessary interference with external objects.

Details regarding the method of the disclosed subject matter are understood from the detailed description above. Generally, however, a method of making a protective sleeve for a medical device having a movable joint is provided, comprising providing a base member comprising a flexible material that satisfies International Organization for Standardization ISO13997 (1999) for cut resistance of at least ISO level 5, the base member has an internal surface and an external surface. A reinforcing member made of the flexible material is coupled to the base member along the internal surface and the external surface of the base member to form a channel. A tubular assembly is formed with the base member and the reinforcing member, the tubular assembly having a first end portion and a second end portion and a length extending therebetween. The channel is disposed at the first end portion of the tubular assembly, the tabular assembly further has an internal cross dimension sized to receive a medical device having a movable joint therein. An adjustment member is inserted within the channel to adjust radially the first end portion of the tubular assembly.

While the disclosed subject matter is described herein in terms of certain preferred embodiments, those skilled in the art will recognize that various modifications and improvements can be made to the disclosed subject matter without departing from the scope thereof. Additional features known in the art likewise can be incorporated. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the various embodiments depicted and claimed, the disclosed subject matter is also directed to other embodiments having any other possible combination of the features disclosed and claimed herein. As such, the particular features presented herein can be combined with each other in other manners within the scope of the disclosed subject matter such that the disclosed subject matter includes any suitable combination of the features disclosed herein. Furthermore, although reference is made to a prosthetic throughout this disclosure, other suitable devices such as orthotics likewise can be used with the apparatus, method, and system disclosed herein. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the apparatus, system and method of the disclosed subject matter without departing from the spirit or scope of the disclosed subject matter. Thus, it is intended that the disclosed subject matter include modifications and variations that are within the scope of the appended claims and their equivalents.

What is claimed is:

1. A protective sleeve for a medical device having a moveable joint, comprising:
 a tubular assembly comprising a flexible material that satisfies ISO 13997:1999 of the International Organization for Standardization for a cut resistance of at least ISO level 5, the tubular assembly having a first end portion, a second end portion, and a length extending therebetween, the tubular assembly including:
a base member made of the flexible material having an internal surface and an external surface,
a reinforcing member made of the flexible material coupled to the base member along the internal surface and the external surface of the base member, wherein the reinforcing member forms a channel at the first end portion of the tubular assembly, the tubular assembly having an internal cross dimension sized to receive a medical device having a moveable joint therein, wherein the reinforcing member extends from the first end portion of the tubular assembly toward the second end portion of the tubular assembly to within approximately 50 percent of a longitudinal dimension of the tubular assembly; and
an adjustment member received in the channel to radially adjust the first end portion of the tubular assembly.

2. A protective sleeve for a medical device having a moveable joint, comprising:
a tubular assembly comprising a flexible material that satisfies ISO 13997:1999 of the International Organization for Standardization for a cut resistance of at least ISO level 5 and that at least comprises ultra-high molecular weight polyethylene, the tubular assembly having a first end portion, a second end portion, and a length extending therebetween, the tubular assembly including:
a base member made of the flexible material having an internal surface and an external surface,
a reinforcing member made of the flexible material coupled to the base member along the internal surface and the external surface of the base member, wherein the reinforcing member forms a channel at the first end portion of the tubular assembly, the tubular assembly having an internal cross dimension sized to receive a medical device having a moveable joint therein; and
an adjustment member received in the channel to radially adjust the first end portion of the tubular assembly.

3. The protective sleeve according to claim 2, wherein the material of the tubular assembly at least meets European Standard EN 388 (2003) testing threshold for an abrasion resistance of at least level 4.

4. The protective sleeve according to claim 2, wherein the material of tubular assembly at least meets European Standard EN 388 (2003) testing threshold for a tear resistance of at least level 4.

5. The protective sleeve according to claim 2, wherein the material of the tubular assembly comprises at least one of cut resistant fabric and tear resistant fabric.

6. The protective sleeve according to claim 2, wherein the material of the tubular assembly comprises Cut-Tex® PRO cut resistant fabric.

7. The protective sleeve according to claim 2, wherein the first end portion of the tubular assembly has an initial circumference ranging from approximately 7 cm to approximately 25 cm when in a substantially cylindrical configuration, and wherein the adjustment member adjusts a transverse dimension of the first end portion of the tubular assembly to a dimension less than the initial circumference.

8. The protective sleeve according to claim 2, wherein the tubular assembly has a longitudinal dimension ranging from approximately 9 cm to approximately 27 cm.

9. The protective sleeve according to claim 8, wherein the reinforcing member of the tubular assembly has a longitudinal dimension less than the longitudinal dimension of the tubular assembly.

10. The protective sleeve according to claim 2, wherein the reinforcing member has an interior surface and an exterior surface, wherein the interior surface of the reinforcing member is coupled to the internal surface and the external surface of the base member.

11. The protective sleeve according to claim 2, wherein the reinforcing member is configured to align with the moveable joint of the medical device.

12. The protective sleeve according to claim 2, wherein the adjustment member comprises at least one of a cord, reinforced elastic web, Velcro device, hook and eye arrangement, draw string, fastening device, latch, or clasp.

13. The protective sleeve according to claim 12, wherein the adjustment member comprises the cord made of at least one of cotton, textured polyester, spun polyester, nylon, polypropylene, and fluoropolymer.

14. The protective sleeve according to claim 12, wherein the adjustment member comprises Spectralon®.

15. The protective sleeve according to claim 2, wherein the channel includes at least one recess for access to the adjustment member for adjusting a transverse dimension of the first end portion of the tubular assembly.

16. The protective sleeve according to claim 2, wherein the adjustment member is self-adjustable with the medical device.

17. The protective sleeve according to claim 2, wherein the second end portion of the tubular assembly comprises an unattached end when used with the medical device.

18. The protective sleeve according to claim 17, wherein the tubular assembly narrows in transverse dimension from the first end portion toward the second end portion.

19. The protective sleeve according to claim 2, wherein the medical device is at least one of a prosthetic device or an orthotic device.

20. The protective sleeve according to claim 2, wherein the protective sleeve is rotatable with respect to the medical device.

21. A protective sleeve system comprising:
a medical device including a member and a moveable joint coupled to the member; and
a protective sleeve comprising:
a tubular assembly comprising a flexible material that satisfies International Organization for Standardization ISO13997 (1999) for a cut resistance of at least ISO level 5, the tubular assembly having a first end portion, a second end portion, and a length extending therebetween, the tubular assembly including:
a base member made of the flexible material having an internal surface and an external surface,
a reinforcing member made of the flexible material coupled to the base member along the internal surface and the external surface of the base member, wherein the reinforcing member forms a channel at the first end portion of the tubular assembly, the tubular assembly having an internal cross dimension sized to receive the medical device having the moveable joint therein; and
an adjustment member received in the channel to radially adjust the first end portion of the tubular assembly,
wherein the length of the tubular assembly is sufficient to extend beyond the moveable joint and the reinforcing member is aligned with the moveable joint when the first end portion of the tubular assembly is in engagement with the member of the medical device.

22. The protective sleeve system according to claim 21, wherein the medical device comprises at least one of a prosthetic device or an orthotic device.

23. The protective sleeve system according to claim 21, wherein the first end portion of the tubular assembly is configured to couple with the medical device and the second end portion of the tubular assembly is extendable beyond the moveable joint of the medical device.

* * * * *